United States Patent [19]

Bell et al.

[11] Patent Number: 5,026,885
[45] Date of Patent: Jun. 25, 1991

[54] PROCESS FOR PREPARING TRANSITION METAL CYCLOPENTADIENYL CARBONYL COMPOUNDS

[75] Inventors: Donald R. Bell; Bruce C. Berris, both of Baton Rouge, La.

[73] Assignee: Ethyl Corporation, Richmond, Va.

[21] Appl. No.: 488,886

[22] Filed: Mar. 6, 1990

[51] Int. Cl.$^5$ .................. C07F 13/00; C07F 11/00; C07F 15/06
[52] U.S. Cl. .................. 556/47; 556/46; 556/48; 556/60; 556/136; 556/142
[58] Field of Search .................. 556/46, 47, 48, 60, 556/136, 142

[56] References Cited

U.S. PATENT DOCUMENTS

| 2,818,417 | 12/1957 | Brown et al. | 260/429 |
| 2,839,552 | 6/1958 | Shapiro et al. | 260/429 |
| 3,127,351 | 3/1964 | Brown et al. | 252/49.7 |

FOREIGN PATENT DOCUMENTS

| 861371 | 2/1961 | United Kingdom | 556/47 |
| 921031 | 3/1963 | United Kingdom | 556/47 |

OTHER PUBLICATIONS

"Reductive Carbonylation Synthesis of Metal Carbonyls, II, Synthesis of Manganese Carbonyl and Group VI-B Metal Carbonyls by the Alkylaluminum Method" J. Am. Chem. Soc. by Podall et al., vol. 82 (1960), pp. 1325-1330.

Primary Examiner—Paul J. Killos
Assistant Examiner—Porfirio Nazario
Attorney, Agent, or Firm—David M. Bunnell

[57] ABSTRACT

Transition metal cyclopentadienyl carbonyl compounds of the formula:

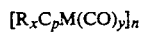

$$[R_xC_pM(CO)_y]_n$$

wherein R is hydrocarbyl, $C_p$ is cyclopentadienyl, M is a transition metal, x is 0 or an integer from 1 to 5, y is an interger from 1 to 7, provided that when x is 2 to 5, R can represent two or more different hydrocarbyl groups and any two R groups can together form a fused ring with the cyclopentadienyl moiety, and n is 1 or 2, are prepared in one step by carbonylating a mixture of
 (i) a transition metal salt of an organic carboxylic acid a β-diketone, or a β-keto ester (ii) a cyclopentadiene compound (iii) and a metal alkyl reducing agent.

14 Claims, No Drawings

PROCESS FOR PREPARING TRANSITION METAL CYCLOPENTADIENYL CARBONYL COMPOUNDS

BACKGROUND

This invention generally relates to the preparation of transition metal cyclopentadienyl carbonyl compounds and more specifically to a one step process for making gasoline engine antiknock compounds such as methylcyclopentadienylmanganese tricarbonyl (MMT).

Cyclopentadienylmanganese tricarbonyls are known antiknock compounds and their preparation and use are described, for example, in U.S. Pat. Nos. 2,818,417, 2,839,552 and 3,127,351 whose teachings are incorporated herein by reference. Two steps are usually required to make such compounds. Either the metal carbonyl is treated with a cyclopentadiene derivative, or a metallocene is prepared from a metal salt and the cyclopentadiene anion and the metallocene is then carbonylated. The starting materials (metallocenes and metal carbonyls) are sometimes expensive to prepare, require high pressure equipment, and/or are available in limited supply. The invention provides an efficient, one-step process for preparing transition metal cyclopentadienyl carbonyls from readily available materials.

SUMMARY

In accordance with this invention, there is provided a process for preparing a transition metal cyclopentadienyl carbonyl compound of the formula:

$$[R_xC_pM(CO)_y]_n$$

wherein R is hydrocarbyl, $C_p$ is cyclopentadienyl, M is a transition metal, x is 0 or an integer from 1 to 5, y is an integer from 1 to 7, and n is 1 or 2, provided that when x is 2 to 5, R can represent two or more different hydrocarbyl groups and any two R groups can together form a fused ring with the cyclopentadienyl moiety; said process comprising:

(A) forming in an organic solvent under an inert atmosphere a mixture comprising (i) a transition metal salt of an organic carboxylic acid, a $\beta$-diketone or a $\beta$-keto ester, (ii) a cyclopentadiene compound and (iii) a metal alkyl reducing agent in mole ratios of about 0.3 to 10 moles of metal alkyl reducing agent and about 1 to 12 moles of cyclopentadiene compound per mole of said transition metal salt, and reacting this mixture under carbon monoxide pressure at a temperature of about 75° to 200° C. so as to form said transition metal cyclopentadienyl carbonyl compound and (B) recovering said transition metal cyclopentadienyl carbonyl compound.

DETAILED DESCRIPTION

Cyclopentadiene compounds suitable for use in the process of the present invention are those described, for example in U.S. Pat. No. 2,839,552. They include cyclopentadiene and hydrocarbyl substituted cyclopentadienes which have one or more $C_1$ to about $C_{12}$ hydrocarbon radicals attached to the ring, so long as the ring contains at least one hydrogen atom. The hydorcarbyl substituents can also together form fused rings with the cyclopentadiene moiety, for example, indene and fluorene and their $C_1$ to $C_{12}$ alkyl substituted and/or hydrogenated derivatives. Preferred are cyclopentadiene itself and lower alkyl substituted ($C_1$ to $C_4$) cyclopentadienes such as methylcyclopentadiene.

The transition metal salts which are effective for use in the process are preferably derived from metals of group VIA, VIIA and VIIIA of the periodic table with atomic numbers of about 25–45, as represented, for example, by molybdenum, manganese, ruthenium, rhodium, and cobalt. The organic anion portion of the salts are derived from aliphatic and aromatic organic carboxylic acids, $\beta$-diketones and $\beta$-ketoesters. The carboxylic acids generally contain from 1 to 12 carbons and the ketones from 5 to 12 carbons. Longer chain compounds can be used but are unnecessary. Examples of these salts are manganese (II) acetate, manganese (II) benzoate, manganese (II) naphthenate, manganese (II) 2-ethylhexanoate, tris(2,4-pentanedione) manganese, tris(2,4-hexanedione) manganese, manganese (II) ethylacetoacetate, cobalt (II) acetate, molybdenyl acetonate and the like. The salts should be anhydrous to avoid the consumption of reducing agent by water.

Effective reducing agents include a wide range of non-halogenated metal alkyls derived, for example, from sodium, aluminum, magnesium and boron. Examples are dialkylmagnesiums, trialkylboranes, alkylaluminums and alkylaluminum alkoxides. Some specific examples of these are diethylmagnesium, triethylborane, diethylaluminum ethoxide, ethylaluminum diethoxide, diisobutylaluminum iso-butoxide, diethylaluminum propoxide and the like. Suitable alkylaluminum compounds are the trialkylaluminum compounds, especially the tri-$C_{1-10}$ alkylaluminum compounds. These include triethylaluminum, trimethylaluminum, tri-n-propylaluminum, triisobutylaluminum, tri-n-butylaluminum, tri-n-hexylaluminum, mixed trialkylaluminum such as methyl diethylaluminum, diethyl propylaluminum, hexyloctyldecylaluminum and the like including mixtures thereof. The most preferred alkylaluminum compound is triethyl aluminum.

The metal alkyl reducing agent can be added undiluted or it can be diluted with an inert solvent. The inert diluents are the same ethers and aliphatic and aromatic hydrocarbons suitable for use as solvents in the reaction. The most preferred inert diluents are toluene and ethyl ether. A useful amount is about 1–30 parts by weight inert solvent per part of metal alkyl compound. A more preferred amount is about 3–20 parts and most preferably about 5–10 parts inert solvent per part metal alkyl compound.

The reactants are mixed together under an inert atmosphere such as argon or nitrogen in a hydrocarbon or ether solvent including mixtures thereof. The hydrocarbon solvents can be aliphatic or aromatic. These include, for example, pentane, hexane, isohexane, heptane, octane, isooctane, nonane, 2-ethylhexane, cyclohexane, benzene, toluene, xylene and the like including mixtures thereof. Suitable ethers include tetrahydrofuran, diethyl ether, and di-$C_{1-2}$ alkyl ethers of mono or polyalkylene glycol such as 1,2-dimethoxyethane, 1,2-diethoxyethane, dimethyl ether of dipropylene glycol, diethyl ether of diethylene glycol and the dimethyl ether of diethylene glycol commonly referred to as "diglyme".

Mixtures of ethers with hydrocarbon solvents in proportions to provide about 0.1 to 10 mole of ether per mole of metal alkyl reducing agent have been found to give effective results and especially, mixtures of diethyl ether in toluene which provide about equivalent amounts of ether and metal alkyl.

The proportions of reducing agent and cyclopentadiene compounds can vary over a wide range to produce the desired product. Suitable proportions can vary from about 0.3 to 10 moles of reducing agent and from about 1 to 12 moles of cyclopentadiene compound per mole of transition metal salt. However, for complete reaction an excess of metal alkyl reducing agent is needed. The preferred ranges are from about 3 to 4 moles of reducing agent and from about 2 to 6 moles of cyclopentadiene compound per mole of transition metal salt. For optimum yields, the ratio is about 3:3:1. The amount of solvent is not critical and can conveniently range from about 2 to 50 parts by weight of the reaction mixture.

Typically, the salt, solvent and cyclopentadiene compound are dried, if necessary, and charged to a reactor under an inert atmosphere of, for example, argon or nitrogen at room temperature. The metal alkyl is added last. The reactor is sealed, purged once or twice with about 200–400 psi of CO, fresh CO is then added to obtain the desired CO pressure of from about 15 to 2,000 psi (preferred about 500 to 1,000 psi) and heating and stirring are started. Alternatively, less CO is added initially and fresh CO is added to the desired pressure after mixture has reached the reaction temperature. The temperature is controlled using a thermocouple and temperature controller. Cooling may be necessary to keep the temperature within the desired range. Suitable temperatures are from 75° to 225° C. and, preferably from about 175° to 200° C. When the carbonylation is complete, as indicated by no further CO uptake (usually from about 15 min to 5 hours), the autoclave is cooled, vented and discharged. The reaction mixture is hydrolyzed with 10% HCl and the organic layer is separated. The aqueous layer is extracted (pentane) and the extracts combined with the organic layer and the layer is dried. The product can be recovered either by distillation or by crystallization with cooling.

The invention is further illustrated by, but is not limited to, the following examples.

EXAMPLE 1

A 300 ml stainless steel autoclave equipped with a stirrer, cooling coils, thermowell, gas inlet and liquid sampling dip tube was charged in a nitrogen filled glovebox with anhydrous manganese II acetate (10 g, 58 mmol), methylcyclopentadiene (MCP) (13.9 g, 174 mmol), 50 ml of toluene solvent, 2.445 g of octane as a GC (gas chromatography) internal standard, and then triethylaluminum (19.9 g, 174 mmol) in 12.9 grams of ethyl ether were added.

The resulting dark solution was sealed in the autoclave. The autoclave was purged twice with 200 psi CO and then pressured with CO to 400 psig. The solution was rapidly stirred and heated to 175° C. The pressure dropped to 220 psig. At 175° C., it was pressured to 800 psi with fresh CO. The pressure did not appear to drop after this point. The autoclave was heated at 175° C./800 psi CO with rapid stirring for 2 hours. It was cooled to 40° C. and a sample (black) was drawn. It was slowly hydrolyzed ( 2x vol., 10% HCl) and the yellow organic phase was extracted with pentane and analyzed by GC. The yield of methylcyclopentadienyl manganese tricarbonyl was 49.3 mmol or 85% on Mn and 45% on consumed MCP.

EXAMPLE 2

An autoclave as in Example 1 was charged in a nitrogen glovebox with anhydrous manganese acetate (2.0 g, 11.6 mmol), 4 equivalents of methylcyclopentadiene (3.7 g, 46.4 mmol), 100 ml of toluene and 1.95 grams of pentadiene as an internal GC standard. The autoclave was sealed, purged with 200 psi CO, pressured to 500 psi CO and rapidly stirred after which 3 equivalents of triethylaluminum (4 g, 34.8 mmol) in 4 g of toluene were added at 25° C. over 50 minutes. The autoclave was heated to 175° C. and pressured to 600 psi with fresh CO. After 2 hours the autoclave was cooled to 30° C. A 1 ml brown, homogeneous sample was drawn and hydrolyzed with 2 ml 10% HCl. The yellow organic layer was extracted with pentane and analyzed by gas chromatography. The yield was 8.9 mmol or 77% on Mn and 56% on consumed MCP.

EXAMPLES 3–8

These examples were conducted in the same general manner of Example 1 with the changes as noted in the following table.

| Ex | Al/Mn Mole Ratio | Solvent | MCP/Mn Mole Ratio | MMT on Mn | Yield % on MCP |
|---|---|---|---|---|---|
| 3[1] | 1.5 | toluene | 6 | 56 | 13 |
| 4 | 3 | ethyl ether | 6 | 81 | 28 |
| 5 | 4 | ethyl ether | 6 | 87 | 28 |
| 6 | 4 | ethyl ether | 1 | 53 | 53 |
| 7[2] | 2 | ethyl ether | 6 | 56 | 21 |
| 8 | 2 | ethyl ether | 1.1 | 40 | — |

[1] 200° C. reaction temperature
[2] 500 psi CO

The results of Examples 1–8 illustrate that a large excess of triethylaluminum to manganese (3:1 molar) should be used to get high conversions of MMT. In other similar preparations, it was found that substituting either (i) isopropyl ether for diethylether (ii) triisobutyl aluminum or mixed magnesium alkyls for triethyl aluminum or (iii) more soluble manganese salts of larger chain acids (hexanoate or napthenoate) for manganese acetate did not significantly effect yields. However, the alkyl group in ethylaluminumethoxides such as diethylaluminumethoxide and ethylaluminumdiethoxide appeared to be utilized more effectively than those in triethyl aluminum.

EXAMPLE 9

A 300 ml stainless steel autoclave was charged in a $N_2$ filled glovebox with anhydrous cobalt (II) acetate (8.0 g, 45.2 mmol), dry pentane (100 ml), cyclopentadiene (9.0 g, 135.6 mmol) monomer and then triethylaluminum (15.5 g, 135.6 mmol). The resulting dark brown, bubbling, heterogeneous solution was sealed in the autoclave which was purged once with 200 psi of CO and then pressured with 400 psi CO. The reaction mixture was heated to 175° C. with rapid stirring. After reaching 175° C., the pressure was increased to 800 psi with additional CO. After 2 hours at 175° C. and 800 psi, the autoclave was cooled to 25° C. and opened in a $N_2$ glovebox. The product mixture was poured into a 250 ml dry Schlenk flask, removed from the drybox and placed under $N_2$. The flask was fitted with a distillation head and a dry-ice chilled receiver. A vacuum of about 0.2 mm Hg was slowly pulled on the liquid with stirring. A red liquid was collected in the dry ice trap after which the flask was heated in a 100° C. oil bath and additional red liquid was collected. Pentane was removed from the distillate at atmospheric pressure through a 5 plate Vigreaux column and the product was then further vacuum distilled (0.1 mm Hg, 55°-60° C.) to recover 3.5 grams of red liquid product (45% yield). NMR and IR data were as expected for cyclopentadienylcobalt dicarbonyl.

EXAMPLE 10

A 300 ml stainless steel autoclave was charged in an argon filled dry box with molybdenyl acetonate (10.0 g, 30.7 mmol), dry pentane (100 ml), cyclopentadiene (6.2 g, 92.1 m mol) and then triethylaluminum (10.5 g, 92.1 mmol) which was added very slowly to avoid an exotherm. The reaction mixture became dark brown. The autoclave was sealed and purged one time with 100 psi CO and then pressured to 600 psi with CO. The reaction mixture was rapidly stirred and heated to 175° C. and then further pressured to 800 psi with CO. After 2 hours at 175° C. and 800 psi, the autoclave was cooled to 25° C., vented, and opened in a dry box. The reaction mixture was transferred to a dry 250 ml Schlenk flask and 50 ml of 10% HCl was slowly added under $N_2$ to hydrolyze the mixture. Air was bubbled through the mixture with replacement of evaporated pentane. After 5 hours warm toluene was added, and the mixture was filtered with suction. The volatiles were removed from the filtrate. The residual oil was dissolved in methylene chloride, and pentane added to cause clouding. Upon cooling, 1.89 grams, 25.5% yield of purple-red crystals separated. NMR and IR data were as expected for $[C_pMo(CO)_3]_2$.

EXAMPLE 11

A 300 ml stainless steel autoclave was charged with 2.00 g manganese (II) acetate (11.6 mmol), 3.07 g cyclopentadiene monomer (46.5 mmol), 70 ml ether, and 4.0 g TEA (35.1 mmol) pre-mixed with some of the ether. The autoclave was sealed and purged with CO. The carbonylation was carried out at 550 psi total pressure and a temperature of 175° C. for two hours. The cooled reactor was vented and the contents transferred to an Erlenmeyer flask. A solution of 10% HCl was added carefully until the salts dissolved. The organic layer was separated and washed with water, dried ($MgSO_4$), filtered and evaporated leaving a red oil. Pentane (100 ml) was added. Cooling to −78° C. for several hours gave 1.10 g (54%) of cyclopentadienylmanganese tricarbonyl product as yellow crystals, mp 65°-69° C.

The foregoing has described a direct, one-step process for obtaining transition metal carbonyl compounds which are useful as free additives. The process uses readily available, materials and can produce significant amounts of product under relatively mild conditions of temperature and pressure.

We claim:

1. A process for preparing a transition metal cyclopentadienyl carbonyl compound of the formula:

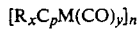

$[R_xC_pM(CO)_y]_n$ wherein R is hydrocarbyl, $C_p$ is cyclopentadienyl, M is a transition metal, x is 0 or an integer from 1 to 5, y is an integer from 1 to 7, and n is 1 or 2, provided that when x is 2 to 5, R can represent two or more different hydrocarbyl groups and any two R groups can together form a fused ring with the cyclopentadienyl moiety; said process comprising forming in an organic solvent under an inert atmosphere a mixture comprising (i) a transition metal salt of an organic carboxylic acid, a β-diketone or a β-keto ester, (ii) a cyclopentadiene compound and (iii) a metal alkyl reducing agent, in mole ratios of about 0.3 to 10 moles of metal alkyl reducing agent and about 1 to 12 moles of cyclopentadiene compound per mole of said transition metal salt, and reacting mixture under carbon monoxide pressure at a temperature of about 75° to 225° C. so as to form said transition metal cyclopentadienyl carbonyl compound.

2. The process of claim 1 wherein said transition metal is a group VIA, VIIA or VIIIA metal having an atomic number of about 25-45 and said cyclopentadiene compound is selected from cyclopentadiene and hydrocarbyl substituted cyclopentadienes which contain at least one hydrogen on the cyclopentadiene ring.

3. The process of claim 2 wherein said hydrocarbon substituted cyclopentadienes have from 1 to 5 $C_1$ to $C_4$ alkyl groups on the ring.

4. The process of claim 2 wherein said transition metal is selected from manganese, cobalt, molybdenum, ruthenium and rhodium.

5. The process of claim 1 wherein the temperature of the reaction is at least about 175° C.

6. The process of claim 1 wherein the temperature of the reaction is from about 175° to 200° C.

7. The process of claim 1 wherein the reaction mixture is carbonylated under an atmosphere of carbon monoxide at a pressure of from about 500 to 1,000 psi.

8. The process of claim 1 wherein the solvent comprises from about 5 to 90 weight percent of the reaction mixture.

9. The process of claim 1 wherein the solvent comprises a hydrocarbon containing from about 0.1 to 1 mole of an ether per mole of metal alkyl reducing agent.

10. The process of claim 1 wherein the salt is manganese (II) acetate, the cyclopentadiene compound is methycyclopentadiene, the solvent is a mixture of toluene and ether, the CO pressure is 500–1,000 psi, the temperature is 175° to 200° C., the reducing agent is triethylaluminum, the mole ratios are about 3 to 4 moles of triethylaluminum and about 2 to 6 moles of methylcyclopentadiene per mole of transition metal, and the transition metal cyclopentadienyl compound is methylcyclopentadienylmanganese tricarbonyl.

11. The process of claim 10 wherein the mole ratios are about 3:3:1.

12. The process of claim 1 wherein said transition metal is manganese.

13. The process of claim 2 wherein said transition metal is manganese and said cyclopentadiene compound is methylcyclopentadiene.

14. The process of claim 13 wherein said reducing agent is triethylaluminum.

* * * * *

UNITED STATES PATENT AND TRADEMARK OFFICE
CERTIFICATE OF CORRECTION

PATENT NO.   : 5,026,885
DATED        : June 25, 1991
INVENTOR(S)  : DONALD R. BELL and BRUCE C. BERRIS It is certified that error appears in the above-identified patent and that said Letters Patent is hereby corrected as shown below:

Column 6, line 14 reads:

-- transition metal salt, and reacting mixture under carbon -- but should read:

"transition metal salt, and reacting _said_ mixture under carbon".

Signed and Sealed this

Twenty-second Day of December, 1992

Attest:

DOUGLAS B. COMER

Attesting Officer

Acting Commissioner of Patents and Trademarks